(12) United States Patent
Pillai et al.

(10) Patent No.: US 10,909,820 B2
(45) Date of Patent: Feb. 2, 2021

(54) HAPTIC AND BIOSENSING HAND MAT

(71) Applicants: Baskaran Pillai, Pittsburgh, PA (US);
Sonja Ann Benkovich, Virginia City, NV (US)

(72) Inventors: Baskaran Pillai, Pittsburgh, PA (US);
Sonja Ann Benkovich, Virginia City, NV (US)

(73) Assignee: Baskaran Pillai, Pittsburgh, PA (US)

( * ) Notice: Subject to any disclaimer, the term of this patent is extended or adjusted under 35 U.S.C. 154(b) by 0 days.

(21) Appl. No.: 16/668,393

(22) Filed: Oct. 30, 2019

(65) Prior Publication Data

US 2020/0134990 A1    Apr. 30, 2020

Related U.S. Application Data

(60) Provisional application No. 62/752,649, filed on Oct. 30, 2018.

(51) Int. Cl.

| | |
|---|---|
| *G08B 6/00* | (2006.01) |
| *G06F 3/16* | (2006.01) |
| *H04R 1/02* | (2006.01) |
| *A61B 5/01* | (2006.01) |
| *A61B 5/00* | (2006.01) |
| *A61B 5/0205* | (2006.01) |
| *A61B 5/024* | (2006.01) |
| *G01K 13/00* | (2021.01) |

(52) U.S. Cl.
CPC .............. *G08B 6/00* (2013.01); *A61B 5/0008* (2013.01); *A61B 5/01* (2013.01); *A61B 5/02055* (2013.01); *G06F 3/165* (2013.01); *H04R 1/028* (2013.01); *A61B 5/024* (2013.01); *G01K 13/002* (2013.01)

(58) Field of Classification Search
CPC ..... A61B 5/0008; A61B 5/01; A61B 5/02055; H04R 1/028; G06F 3/165; G01K 13/002; G08B 6/00
USPC ............................................ 340/407.1, 407.3
See application file for complete search history.

(56) References Cited

U.S. PATENT DOCUMENTS

| | | | | |
|---|---|---|---|---|
| 5,614,887 | A * | 3/1997 | Buchbinder | G08B 25/016 340/573.1 |
| 5,974,262 | A | 10/1999 | Fuller et al. | |
| 6,461,316 | B1 | 10/2002 | Lee et al. | |
| 9,390,630 | B2 * | 7/2016 | Daniels | G09B 15/00 |
| 9,615,746 | B2 | 4/2017 | Horseman | |
| 9,921,726 | B1 | 3/2018 | Sculley et al. | |
| 10,058,476 | B2 | 8/2018 | Baxter et al. | |
| 10,065,114 | B2 | 9/2018 | Goetgeluk et al. | |
| 10,182,964 | B2 | 1/2019 | Snow | |
| 10,416,768 | B2 | 9/2019 | Khoshkava et al. | |
| 10,416,769 | B2 | 9/2019 | Ofek et al. | |
| 2002/0111777 | A1 | 8/2002 | David | |

(Continued)

*Primary Examiner* — Ojiako K Nwugo
(74) *Attorney, Agent, or Firm* — Dunlap Bennett & Ludwig, PLLC

(57) ABSTRACT

A haptic mat includes a mat surface, a plurality of haptic vibrators, and a computing device. The plurality of haptic vibrators are disposed on the mat surface within a boarder representing at least one human hand. The computing device is electrically coupled to the plurality of haptic vibrators. The computing device includes at least a processor and a memory. The processor controls the activation of each of the plurality of haptic vibrators independently of one another. The processor further controls a level of vibration of each of the plurality of haptic vibrators.

15 Claims, 4 Drawing Sheets

(56) References Cited

U.S. PATENT DOCUMENTS

| | | |
|---|---|---|
| 2002/0132092 A1 | 9/2002 | Wagner |
| 2002/0198473 A1 | 12/2002 | Kumar |
| 2003/0158692 A1 | 8/2003 | Tamada |
| 2009/0062076 A1* | 3/2009 | Curley .................. A63B 26/00 482/23 |
| 2009/0312817 A1 | 12/2009 | Hogle et al. |
| 2010/0016125 A1* | 1/2010 | Bellandi .................. A63B 6/00 482/4 |
| 2010/0076347 A1 | 3/2010 | McGrath et al. |
| 2012/0215076 A1 | 8/2012 | Yang et al. |
| 2013/0225915 A1 | 8/2013 | Redfield et al. |
| 2013/0245480 A1* | 9/2013 | Crockford ............ A61B 5/6825 600/521 |
| 2014/0349257 A1 | 11/2014 | Connor |
| 2015/0317910 A1 | 11/2015 | Daniels |
| 2017/0128816 A1* | 5/2017 | DeMarch .............. A61B 5/6892 |
| 2017/0164900 A1 | 6/2017 | Johnson et al. |
| 2017/0209742 A1 | 7/2017 | Merkel et al. |
| 2018/0020858 A1 | 1/2018 | Gloeckl |

\* cited by examiner

HAPTIC AND BIOSENSING HAND MAT

CROSS-REFERENCE TO RELATED APPLICATION

This application claims the benefit of priority of U.S. provisional application No. 62/752,649, filed Oct. 30, 2018, the contents of which are herein incorporated by reference.

BACKGROUND OF THE INVENTION

The present invention relates to stimulating targeted brain areas and, more particularly, to a haptic mat for stimulating targeted brain areas.

Commercial devices aim to enhance brain functionality through games, tDCS (transcranial Direct Current Stimulation) which applies electrical current to the head area, and other mental concentration methods. However, these mechanisms often have a general effect on the brain and do not target area-specific brain functions. These techniques and devices are also not unilaterally appropriate for general use, particularly with children, elderly or those with specific medical conditions.

Individuals additionally have difficulty complying with purely mental-based cognitive brain development methods, such as visualizations or meditations, especially when they are non-game based due to attentional difficulties of the individual and the absence of objective performance metrics which inspire the individual to continue with the protocol.

As can be seen, there is a need for improved devices for enhancing brain functionality.

SUMMARY OF THE INVENTION

In one aspect of the present invention, a haptic hand mat comprises: a mat surface; a plurality of haptic vibrators disposed on the mat surface within a boarder representing at least one human hand; and a computing device electrically coupled to the plurality of haptic vibrators, the computing device comprising at least a processor and a memory, wherein the processor controls an activation of each of the plurality of haptic vibrations independent of one another and a level of vibration of each of the plurality of haptic vibrators.

In another aspect of the present invention, a haptic hand mat comprises: a mat surface; a plurality of haptic vibrators disposed on the mat surface within a boarder representing at least one human hand; at least one biometric sensor disposed on the mat surface within the boarder; and a computing device electrically coupled to the plurality of haptic vibrators and the at least one biometric sensor, the computing device comprising at least a processor and a memory, wherein the processor controls an activation of each of the plurality of haptic vibrations independent of one another and a level of vibration of each of the plurality of haptic vibrators, and the computing device records biometric readings of the at least one biometric sensor.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a programmable haptic, bio-sensory hand mat for cognitive improvement. Using haptic stimulation in the hands, accompanying an audio guided neuro-cognitive enhancement protocol, the hands mat activates specific targets in the brain and increases fidelity to the accompanying brain development method. Infrared biometric sensors may monitor bodily responses to the protocol.

By using a mat on which the palms of the hands are placed, haptic stimulation in specific sequences is applied to areas of the palms and fingers. Through the desired haptic sequence and the accompanying guided audio and/or visual protocol, the brain more easily shifts into the desired synchronization, brainwave inducement or area-specific activation state. The hands mat activates brain areas while it monitors real-time biometric feedback via infrared sensors without attaching anything to the head area or body. Any discomfort from the user can be addressed by simply lifting the hands from the mat. The mat is easily portable being able to be rolled or folded and kept hygienic with periodic wiping with sanitizing wipes.

Figure 1:
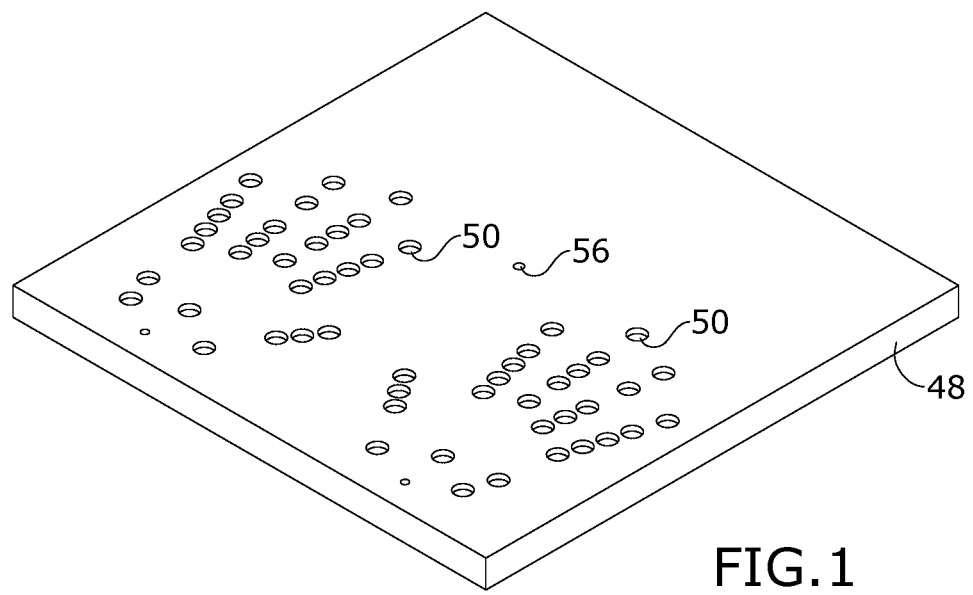
FIG. 1 is a perspective view of an embodiment of the present invention.
Figure 2:
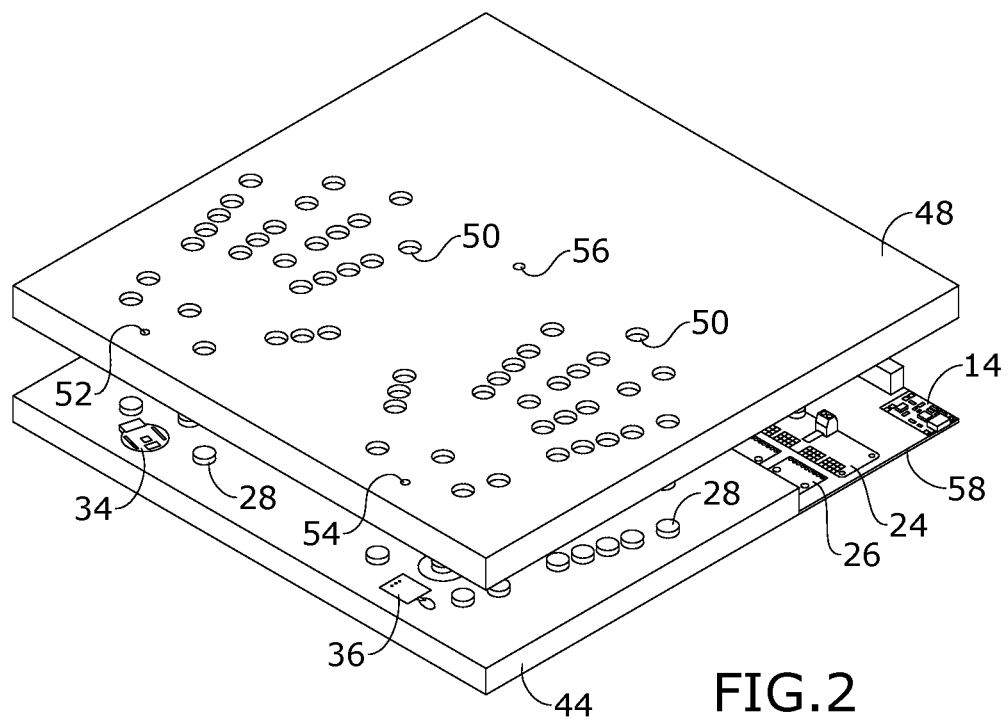
FIG. 2 is a partial exploded view of an embodiment of the present invention.
Figure 3:
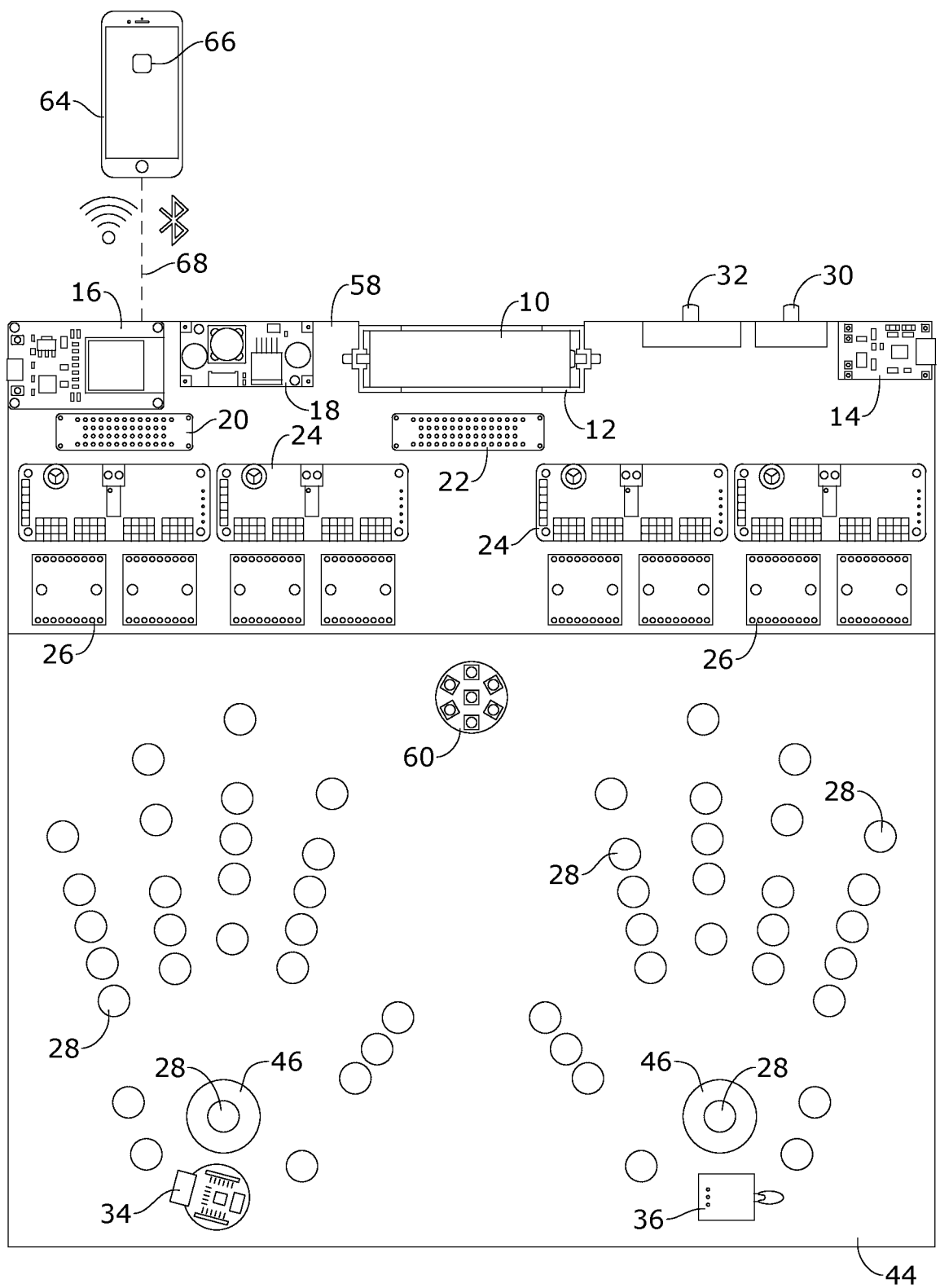
FIG. 3 is a schematic view of an embodiment of the present invention.
Figure 4:
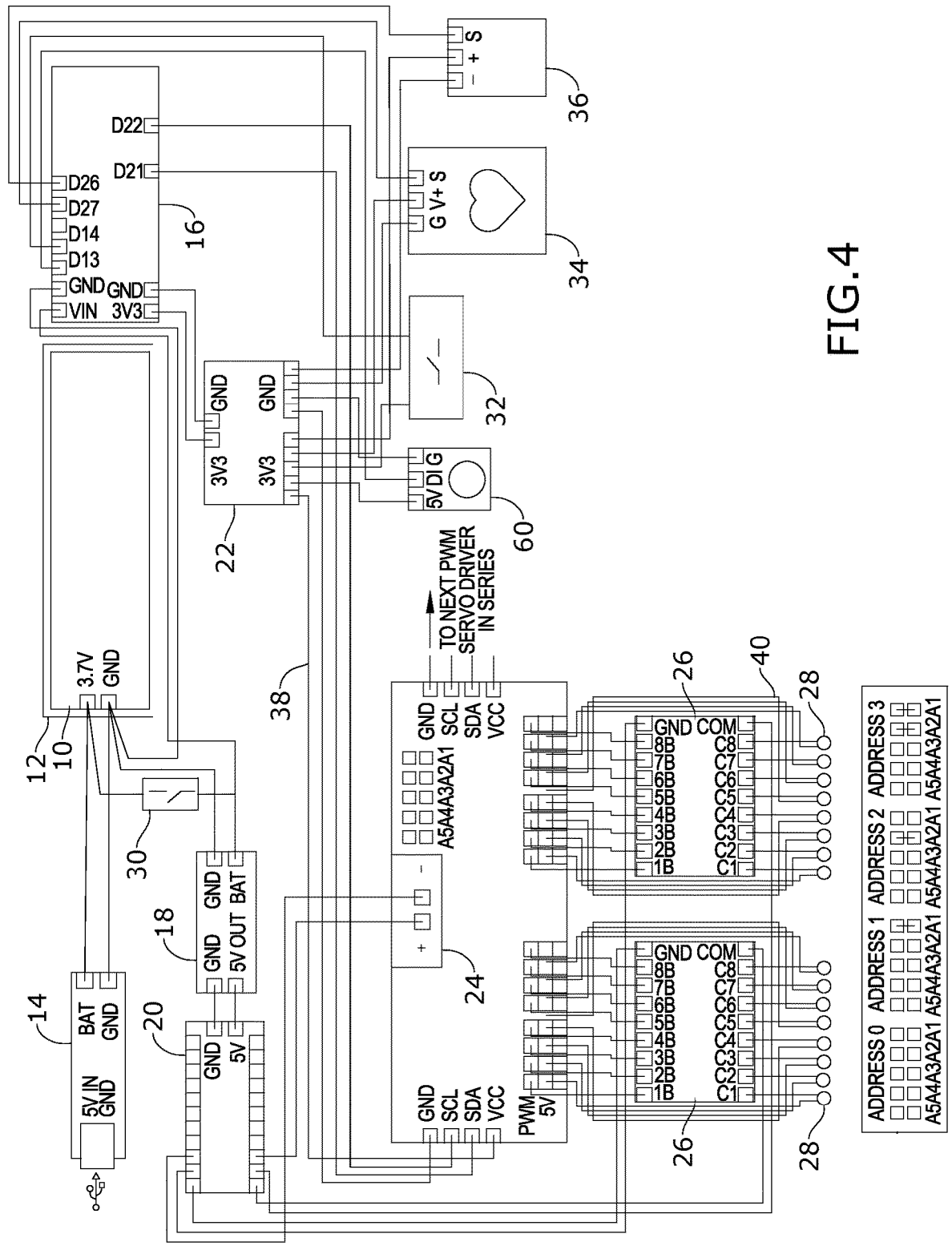
FIG. 4 is a wiring diagram of an embodiment of the present invention.
Figure 5:
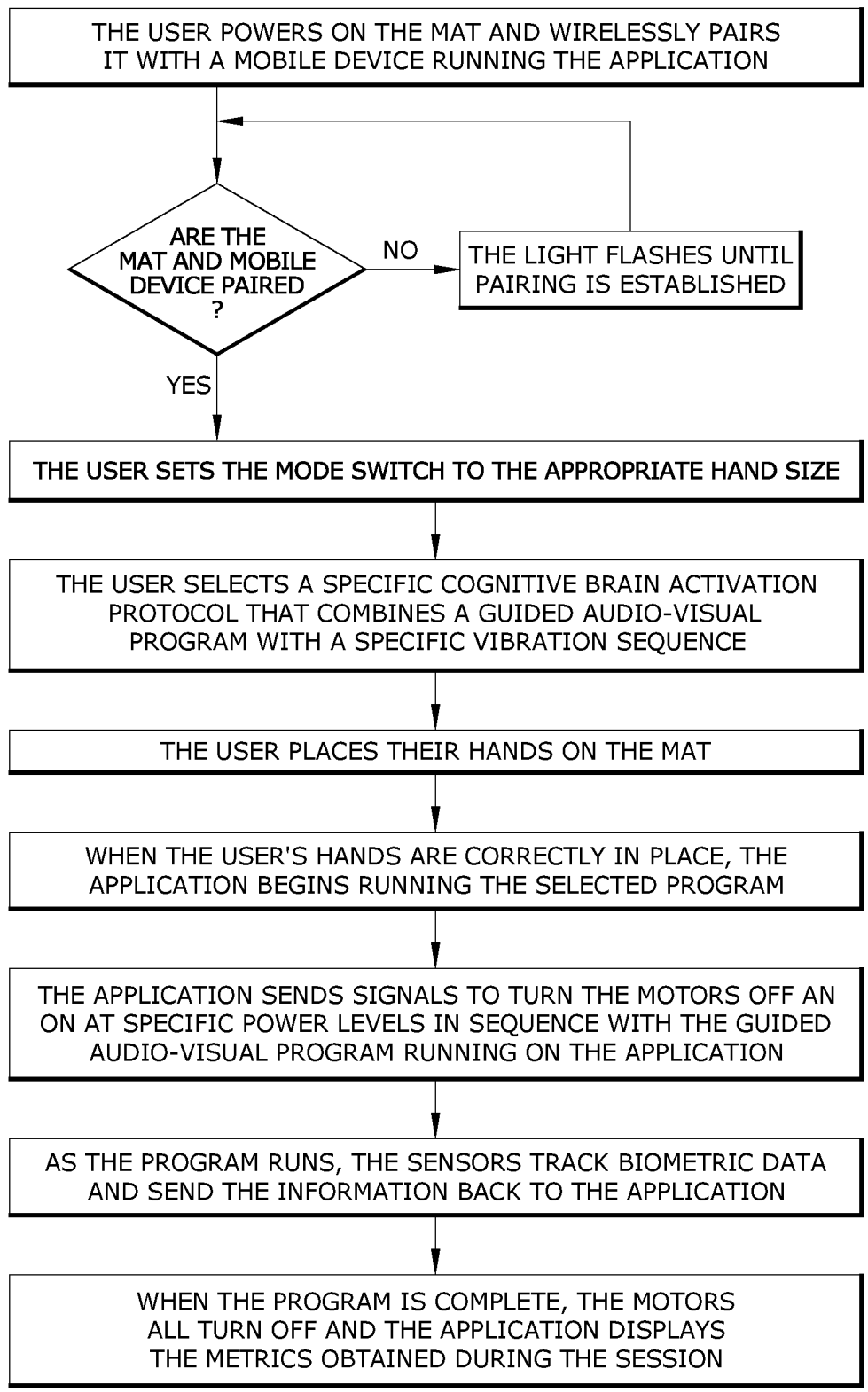
FIG. 5 is a flow chart of an embodiment of the present invention.

Referring to FIGS. 1 through 5, the present invention includes a haptic mat. The haptic mat includes a mat surface 48, a plurality of haptic vibrators 28, and a computing device 16. The plurality of haptic vibrators 28 are disposed on the mat surface 28 within a boarder representing at least one human hand. The computing device 16 is electrically coupled to the plurality of haptic vibrators 28. The computing device 16 includes at least a processor and a memory. The processor controls the activation of each of the plurality of haptic vibrators 28 independently of one another. The processor further controls a level of vibration of each of the plurality of haptic vibrators 28.

In certain embodiments, the plurality of haptic vibrators 28 include at least one haptic vibrator 28 corresponding with each finger and thumb of the human hand, and at least one haptic vibrator 28 corresponding with a palm of the human hand. In further embodiments, the at least one haptic vibrator 28 corresponding with each finger and thumb of the human hand is at least three haptic vibrators 28 corresponding with each finger and thumb of the human hand.

The present invention may be used with one hand or both hands. For example, the plurality of haptic vibrators 28 may include a first set of haptic vibrators 28 disposed within a boarder representing a right hand and a second set of haptic vibrators 28 disposed within a boarder representing a left hand. In certain embodiments, the present invention may accommodate different hand sizes. For example, the present invention may include more than three haptic vibrators 28 per finger and thumb. Based on the hand size selected, only the haptic vibrators 28 that correspond with the selected hand size are used. A hand size switch 32 may be used to select different hand sizes (Small, Medium and Large).

The computing device 16 of the mat may further include a wireless communication interface. For example, the wireless communication interface may include a WIFI adapter, BLUETOOTH™ and the like. In such embodiments, the present invention communicates with a remote computing device 64 over a wireless connection 68. The remote computing device 64 may include a laptop, desktop, or smart device, such as a smart phone or a tablet. In certain embodiments, a smart device may include an application 66 loaded on the smart device's memory. The application 66 may be used to control the haptic mat. For example, a protocol may be selected using the application 66. The protocol may include a digital file including a sequence of activation of the haptic vibrators 28. The protocol is wirelessly transferred to the computing device 16 of the haptic mat. The computing device 16 follows the protocol by initiating two commands for each haptic vibrator 28: ON (with accompanying power level) and OFF.

The present invention may further utilize a speaker and/or a display screen. In such embodiments, the protocol may include an audio/video file of a cognitive improvement protocol that uses sounds and visualizations and a sequence of activations each comprising a level of activation for the plurality of haptic vibrators 28. The sequence is linked with the audio/video file such that the audio/video file is played on the speaker and displayed simultaneous with the sequence of activations of the plurality of haptic vibrators 28.

In certain embodiments, the present invention may include at least one biometric sensor 34, 36 on the mat surface 48 disposed within the boarder. The computing device 16 records biometric readings of the at least one biometric sensor 34, 36. The mat includes at least one biometric sensor 34, 36 and may include a plurality of biometric sensors 34, 36, such as but not limited to a temperature sensor 34 and a heart rate sensor 36. In certain embodiments, the biometric sensors may also detect galvanic skin responses, thermal imaging, and other near infrared (NIR) detections such as blood oxygenation. The biometric readings may be wirelessly transferred to the remote computing device 64. Sensory input readings from the heart rate sensor 34 and temperature sensor 36 are queried by the application 66 at the start and end of the program, as well as at junctures during the programs run when all haptic vibrators 28 are in the off state.

In certain embodiments, the present invention may include a foam mat 44 and a cover disposed over the foam mat 44. The cover may include the mat surface 48. The plurality of haptic vibrators 28 may be coupled to the foam mat 44 and protrude through corresponding vibrator openings 50 of the cover. An additional foam circle 46 may be mounted to elevate the haptic vibrator 28 which is placed at the palm of the hand to ensure good contact. The temperature sensor 34 and the heart rate sensor 36 may also be coupled to the foam mat 44. A temperature sensor opening 52 is formed through the cover over the temperature sensor 34 and a heart rate sensor opening 54 is formed through the cover over the heart rate sensor 36.

The present invention may include a mounting board 58 in which the computing device 16 is mounted. A battery 10 is encased in a battery holder 12 and recharged by a charger 14. In certain embodiments, the rechargeable battery 10 can be charged via a mini solar panel or by kinetic energy by shaking the mat vigorously for 60 seconds. The power switch 30 connects current circuits from the battery 10 to a 5V Regulator 18 and the computing device 16 which further flows to other components through 5V breakout 20 and 3V breakout 22. Electrical wiring 38 may electrically connected the breakouts 20, 22 to the pwm servo drivers 24. Motor wires 40 run from the pwm servo drives 24 to the motor drivers 26 and haptic vibrators 28. The motor drivers 26 drive the haptic vibrators 28. The electronic components may be shielded in an enclosure.

The commands sent to computing device 14 are of two kinds: ON with a specific power setting for each motor, or OFF. When the command is sent, it flows from the computing device 14 through the regulator 18 and the breakouts 20, 22 to the motor drivers 26. Additionally, the pwm servo drivers 24 are powered through the breakouts 20, 22 which is connected to the battery 10. In certain embodiment, the present invention includes four pwm servo motor drivers 24 which drive two motor drivers 26 each. These four pwm servo motor drivers 24 are connected to the 5V breakout 20, which acts as a hub for commands from the processor. In total there may be eight motor drivers 26 each having the ability to power eight haptic vibrators 28. Fifty-four haptic vibrators 28 may receive instructions as outlined above to power on and off at specific power levels. The processor also controls a light 60 that shines through an opening 56 of the cover. The light 60 indicates to the user if the remote computer 64 is properly paired with the mat or if the user has correctly placed the hands on the mat. In certain embodiments, the biometric sensors 34, 36 provide heart rate and temperature indications which are programmatically queried through the processor and the data is sent back to the remote computing device 64 via the application 66.

The computing device 16 may detect whether the user's hands are properly placed on the mat using an infrared sensor at each haptic vibrators 28 or by pressure placed on the haptic vibrator 28 itself. When the correct hand placement is obtained, the light 60 turns on, indicating to the user to proceed. A signal is also sent back to the mobile application 66 to indicate on the application 66 that the hands are in place and the protocol is initiated. Alternatively, the light 60 indicates to the user that the mat and the remote computing device 64 are properly paired. The user then sets the mode switch to the appropriate hand size. The user selects the cognitive brain activation protocol that combines a guided audio-visual program with a specification vibration sequence. The user places their hands on the mat. When the user's hands are correctly in place, the application begins running the selected program. The application sends signals to turn the haptic vibrators 28 off and on at specific power levels in sequence with the guided audio/visual program running on the application. The haptic vibrators 28 vibrate in frequency, duration and sequence according to the guided cognitive brain activation protocol, enhancing the focus and enjoyment of the audio and/or visual output of the remote computing device 64. The infrared monitoring biometric sensors 34, 36 detect skin, pulse and blood flow changes during the practice session, and relay the information back to the remote computing device 64. When the program is complete, the haptic vibrators 28 all turn off and the application displays the metrics obtained by the sensors 34, 36 during the session.

The hand mat of the present invention works in a multi-mat configuration for use in settings such as a classroom. From one controlling program on a mobile app, multiple mats maybe activated. As the PHONEMIC INTELLIGENCE™ (PI) cognitive protocol activates specific brain areas associated with learning, a teacher may implement a PI brain exercise, and all of the mats in the classroom may simultaneously activate according to protocol. The PHONEMIC INTELLIGENCE™ (PI) protocol along with the hands mat creates an easy way to stimulate targeted brain areas by correlating the brain's natural nerve routes to the hands and applying haptic vibrations on these pathways. Through applying vibrations to the left and right hands, desired brainwave states can be induced including hemispheric synchronization and brainwave activation of area-specific functions. The external, physical application of stimulation to the hands augments neuro-cognitive development protocols, for example, memory enhancement exercises, by generating conducive brainwaves in specific areas. The mechanical targeted stimulation via the haptic motors overcomes many issues of tDCS (transcranial Direct Current Stimulation) which works primarily on surface neocortex stimulation and without refined capability to activate brain specific areas or internal brain structures.

It should be understood, of course, that the foregoing relates to exemplary embodiments of the invention and that modifications may be made without departing from the spirit and scope of the invention as set forth in the following claims.

What is claimed is:

1. A haptic hand mat comprising:
a mat surface;
a plurality of haptic vibrators disposed on the mat surface within a boarder representing at least one human hand; and
a computing device electrically coupled to the plurality of haptic vibrators, the computing device comprising at least a processor and a memory, wherein the processor controls an activation of each of the plurality of haptic vibrations independent of one another and a level of vibration of each of the plurality of haptic vibrators.

2. The haptic hand mat of claim 1, wherein the activation and the level of vibration are based on a protocol loaded on the memory.

3. The haptic hand mat of claim 1, wherein the plurality of haptic vibrators comprises at least one haptic vibrator corresponding with each finger and thumb of the human hand, and at least one haptic vibrator corresponding with a palm of the human hand.

4. The haptic hand mat of claim 3, wherein the at least one haptic vibrator corresponding with each finger and thumb of the human hand is at least three haptic vibrators corresponding with each finger and thumb of the human hand.

5. The haptic hand mat of claim 1, wherein the plurality of haptic vibrators comprise a first set of haptic vibrators disposed within a boarder representing a right hand and a second set of haptic vibrators disposed within a boarder representing a left hand.

6. The haptic hand mat of claim 2, further comprising at least one biometric sensor disposed on the mat surface within the boarder, wherein the computing device records biometric readings of the at least one biometric sensor.

7. The haptic hand mat of claim 6, wherein the at least one biometric sensor is a plurality of biometric sensors comprising a temperature sensor and a heart rate sensor.

8. The haptic hand mat of claim 6, wherein the computing device further comprises a wireless communication interface.

9. The haptic hand mat of claim 8, wherein the protocol is wirelessly transferred to the computing device from a remote computing device.

10. The haptic hand mat of claim 9, wherein the biometric readings are wirelessly transferred to the remote computing device.

11. The haptic hand mat of claim 2, further comprising a speaker, wherein the protocol comprises an audio file and a sequence of activations each comprising a level of activation for the plurality of haptic vibrators, wherein the sequence is linked with the audio file such that the audio file is played on the speaker simultaneous with the sequence of activations of the plurality of haptic vibrators.

12. The haptic hand mat of claim 11, wherein the computing device further comprises a wireless communication interface and the speaker is part of a remote computing device.

13. A haptic hand mat comprising:
a mat surface;
a plurality of haptic vibrators disposed on the mat surface within a boarder representing at least one human hand;
at least one biometric sensor disposed on the mat surface within the boarder; and
a computing device electrically coupled to the plurality of haptic vibrators and the at least one biometric sensor, the computing device comprising at least a processor and a memory, wherein the processor controls an activation of each of the plurality of haptic vibrations independent of one another and a level of vibration of each of the plurality of haptic vibrators, and the computing device records biometric readings of the at least one biometric sensor.

14. The haptic hand mat of claim 13, wherein the at least one biometric sensor is a plurality of biometric sensors comprising a temperature sensor and a heart rate sensor.

15. The haptic hand mat of claim 13, further comprising a speaker, wherein a protocol comprises an audio file and a sequence of activations each comprising a level of activation for the plurality of haptic vibrators, wherein the sequence is linked with the audio file such that the audio file is played on the speaker simultaneous with the sequence of activations of the plurality of haptic vibrators.

* * * * *